US005647377A

United States Patent [19]

Shinabarger

[11] Patent Number: 5,647,377

[45] Date of Patent: Jul. 15, 1997

[54] NOISE SUPPRESSOR APPARATUS

[76] Inventor: Joe E. Shinabarger, P.O. Box 252, Carson City, Mich. 48811

[21] Appl. No.: 617,572

[22] Filed: Mar. 19, 1996

[51] Int. Cl.[6] ..... A61F 11/00

[52] U.S. Cl. ..... 128/864; 128/867

[58] Field of Search ..... 128/864–867; 2/209, 423; 181/129

[56] References Cited

U.S. PATENT DOCUMENTS 1,312,493 8/1919 Theis ..... 128/867

2,437,049 3/1948 Salisbury ..... 128/867

3,862,451 1/1975 Miller ..... 2/209

4,441,576 4/1984 Allen ..... 128/867

*Primary Examiner*—Michael A. Brown

[57] ABSTRACT

A noise suppressor apparatus including a cylindrical member having an open upper end, a closed lower end, a cylindrical side wall therebetween, and a hollow interior. The closed lower end has an aperture formed therethrough. A noise suppressing portion is dimensioned for placement within the hollow interior of the cylindrical member.

7 Claims, 3 Drawing Sheets

NOISE SUPPRESSOR APPARATUS

BACKGROUND OF THE INVENTION

1. Field of the Invention

The present invention relates to a noise suppressor apparatus and more particularly pertains to reducing audible level of coughs, sneezes, or the like with a noise suppressor apparatus.

2. Description of the Prior Art

The use of face filters is known in the prior art. More specifically, face filters heretofore devised and utilized for the purpose of filtering inhaled air are known to consist basically of familiar, expected and obvious structural configurations, notwithstanding the myriad of designs encompassed by the crowded prior art which have been developed for the fulfillment of countless objectives and requirements.

By way of example, U.S. Pat. No. 3,719,188 to Fisher et al. discloses a cough filter.

U.S. Pat. No. 5,357,947 to Adler discloses a face mask.

U.S. Pat. No. 4,004,584 to Geaney discloses a facially-worn breathing filter.

U.S. Pat. No. 4,240,420 to Riaboy discloses a nose and mouth filter combination.

U.S. Pat. No. 4,893,421 to Folks discloses a hunting shoe noise suppressor.

U.S. Pat. No. 4,719,911 to Carrico discloses an air filter mask with mouth retention means.

While these devices fulfill their respective, particular objective and requirements, the aforementioned patents do not describe a noise suppressor apparatus for reducing audible level of coughs, sneezes, or the like.

In this respect, the noise suppressor apparatus according to the present invention substantially departs from the conventional concepts and designs of the prior art, and in doing so provides an apparatus primarily developed for the purpose of reducing audible level of coughs, sneezes, or the like.

Therefore, it can be appreciated that there exists a continuing need for new and improved noise suppressor apparatus which can be used for reducing audible level of coughs, sneezes, or the like. In this regard, the present invention substantially fulfills this need.

SUMMARY OF THE INVENTION

In the view of the foregoing disadvantages inherent in the known types of face filters now present in the prior art, the present invention provides an improved noise suppressor apparatus. As such, the general purpose of the present invention, which will be described subsequently in greater detail, is to provide a new and improved noise suppressor apparatus and method which has all the advantages of the prior art and none of the disadvantages.

To attain this, the present invention essentially comprises a cylindrical member having an open upper end, a closed lower end, a cylindrical side wall therebetween, and a hollow interior. The closed lower end has an aperture formed therethrough. The cylindrical side wall is comprised of a rigid interior layer and a soft foam outer layer. The closed lower end is comprised of a soft foam layer. The device includes a circular mouth member having an annular recess formed in a lower surface thereof. The annular recess is secured to the open upper end of the cylindrical member. The circular mouth member has an opening therethrough. The device includes a handle portion having a generally U-shaped configuration. Free ends of the handle portion are secured to the cylindrical side wall of the cylindrical member upwardly of the closed lower end thereof. The device includes a noise suppressing portion comprised of a planar member having a plurality of apertures formed therethrough. The planar member has a short lower end and a long upper end. The planar member has a straight side edge and an angular lower edge whereby a width of the planar member gradually increases from the short lower end to the long upper end. The short lower end has a disk member secured thereto. The disk member has a plurality of apertures therethrough The noise suppressing portion is dimensioned for placement within the hollow interior of the cylindrical member with the planar member in a spiraled configuration whereby the disk member positioned within the aperture in the closed lower end of the cylindrical member.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved noise suppressor apparatus which has all the advantages of the prior art face filters and none of the disadvantages.

It is another object of the present invention to provide a new and improved noise suppressor apparatus which may be easily and efficiently manufactured and marketed.

It is a further object of the present invention to provide a new and improved noise suppressor apparatus which is of durable and reliable construction.

An even further object of the present invention is to provide a new and improved noise suppressor apparatus which is susceptible of a low cost of manufacture with regard to both materials and labor, and which accordingly is then susceptible of low prices of sale to the consuming public, thereby making such a noise suppressor apparatus economically available to the buying public.

Still yet another object of the present invention is to provide a new and improved noise suppressor apparatus which provides in the apparatuses and methods of the prior art some of the advantages thereof, while simultaneously overcoming some of the disadvantages normally associated therewith.

Even still another object of the present invention is to provide a new and improved noise suppressor apparatus for reducing audible level of coughs, sneezes, or the like.

Lastly, it is an object of the present invention to provide a new and improved noise suppressor apparatus including a cylindrical member having an open upper end, a closed lower end, a cylindrical side wall therebetween, and a hollow interior. The closed lower end has an aperture formed therethrough. A noise suppressing portion is dimensioned for placement within the hollow interior of the cylindrical member.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 2:
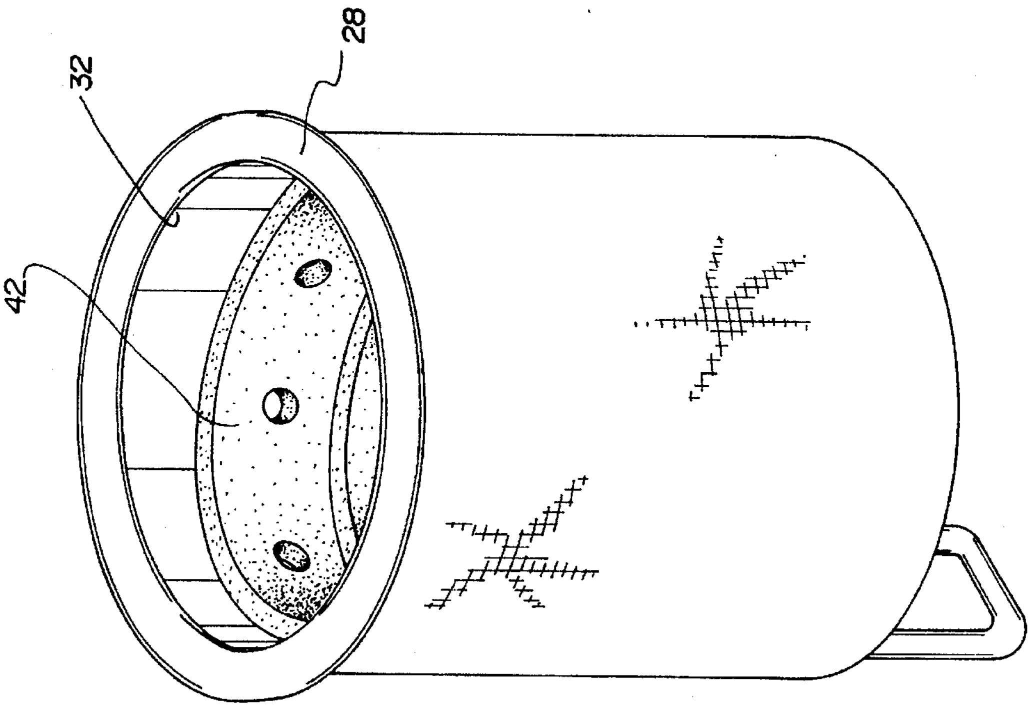
FIG. 2 is a perspective view of the present invention in an inverted arrangement.
Figure 1:
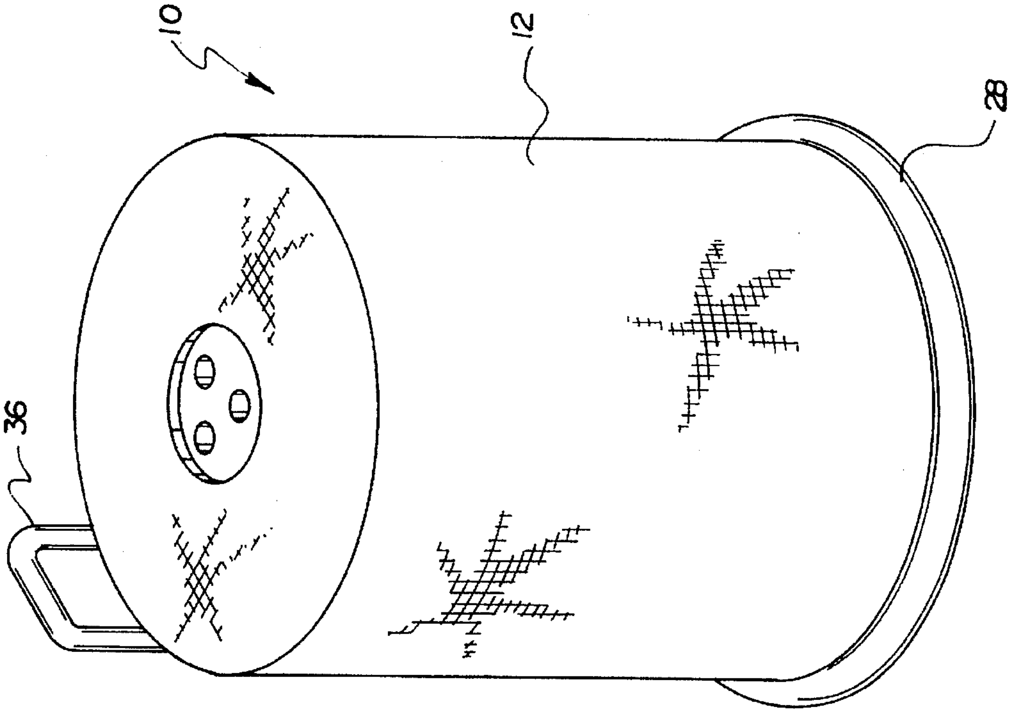
FIG. 1 is a perspective view of the preferred embodiment of the noise suppressor apparatus constructed in accordance with the principles of the present invention.
Figure 4:
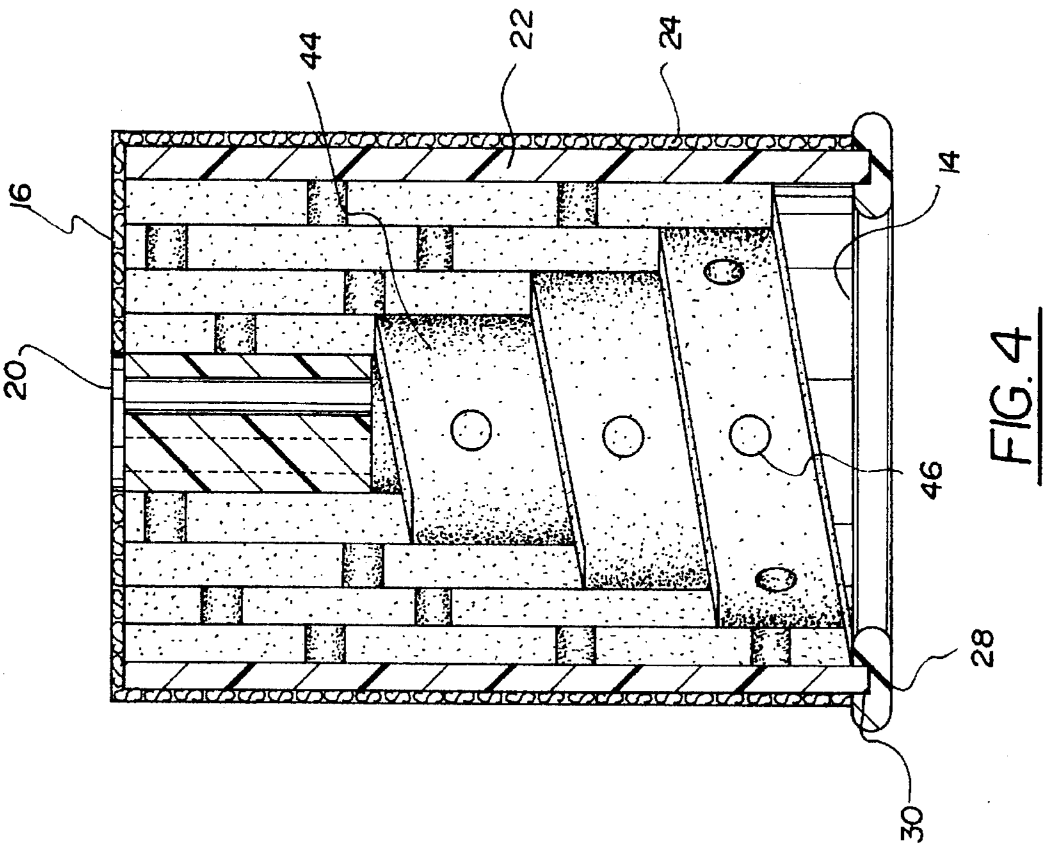
FIG. 4 is a cross-sectional view as taken along line 4—4 of FIG. 3.
Figure 3:
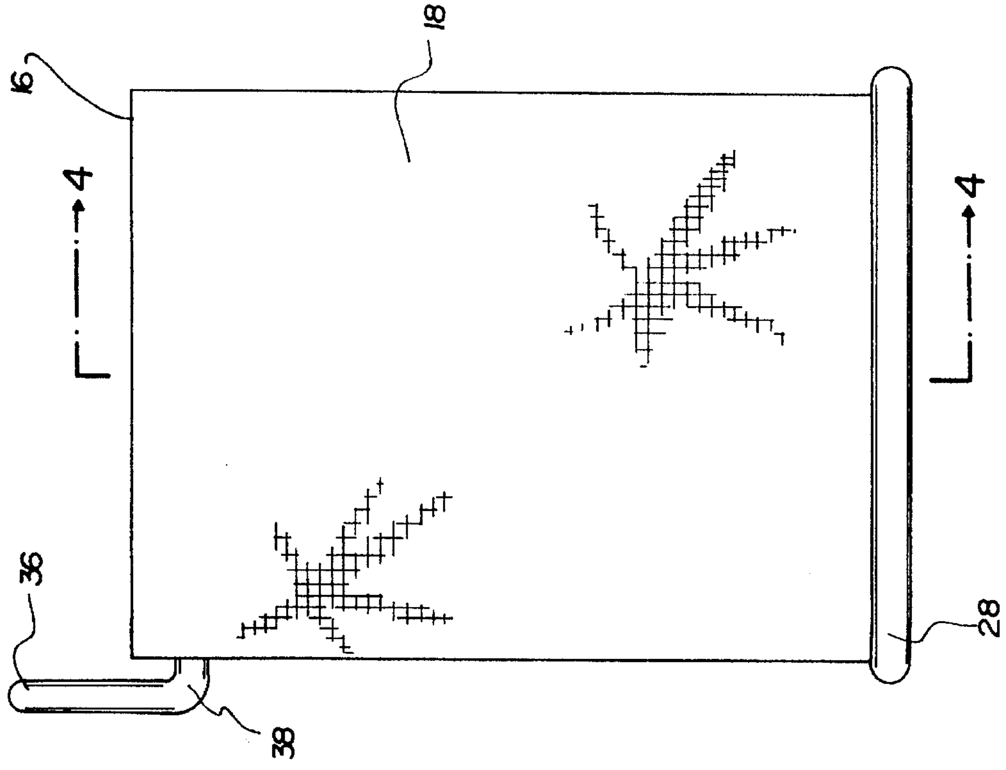
FIG. 3 is a side elevation view of the present invention.
Figure 5:
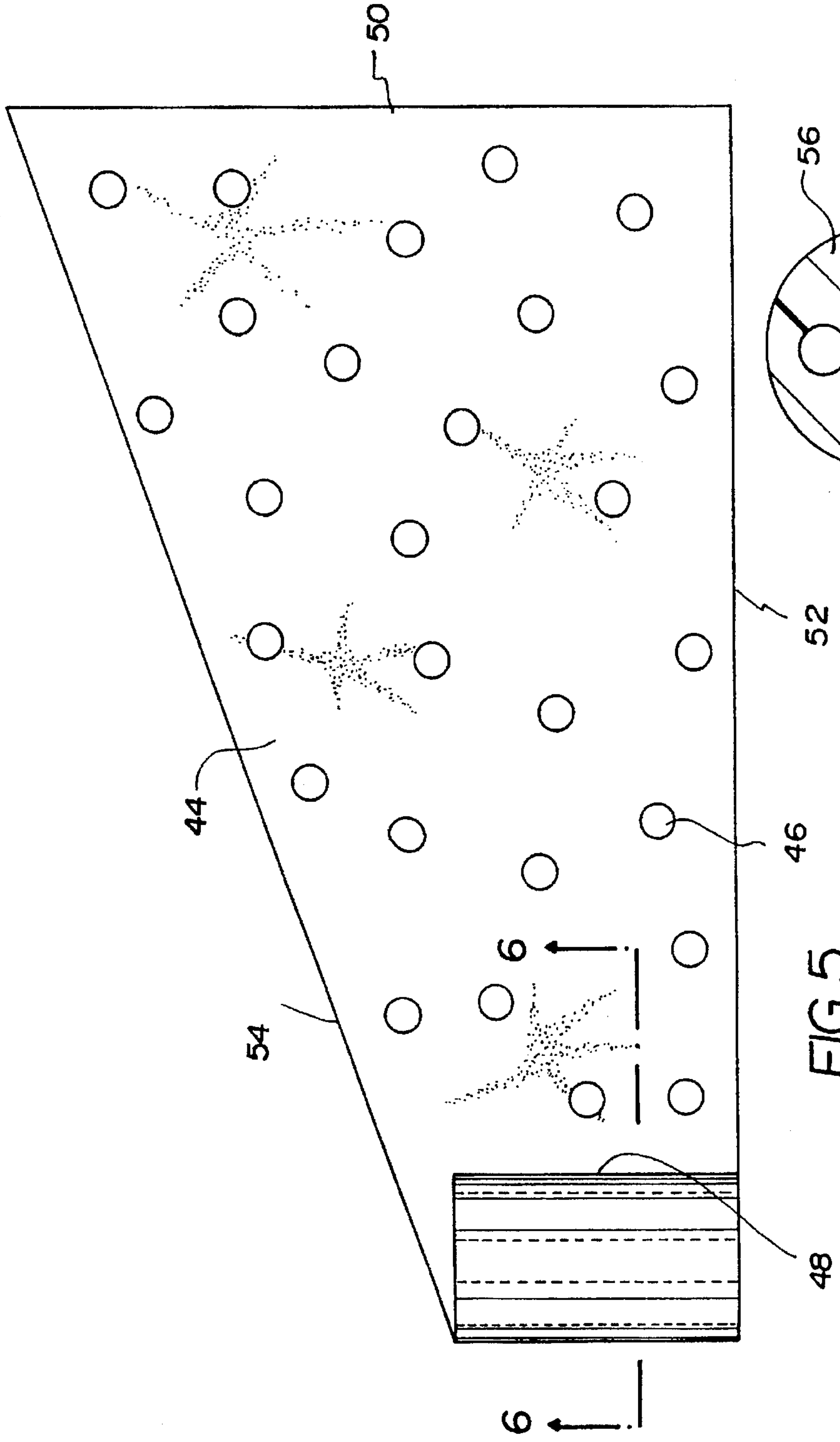
FIG. 5 is a view of the noise suppressing portion in an open configuration.
Figure 6:
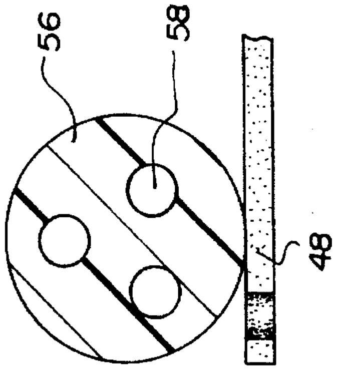
FIG. 6 is a plan view of the lower end of the noise suppressing portion of the present invention shown in cross-section along line 6—6 of FIG. 5.

With reference now to the drawings, and in particular, to FIGS. 1–6 thereof, the preferred embodiment of the new and improved noise suppressor apparatus embodying the principles and concepts of the present invention and generally designated by the reference number 10 will be described.

Specifically, it will be noted in the various Figures that the device relates to a new and improved noise suppressor apparatus for reducing audible level of coughs, sneezes, or the like. In its broadest context, the device consists of a cylindrical member, a mouth member, a handle portion, and a noise supporting portion. Such components are individually configured and correlated with respect to each other so as to attain the desired objective.

The device 10 includes a cylindrical member 12 having an open upper end 14, a closed lower end 16, a cylindrical side wall 18 therebetween, and a hollow interior. The closed lower end 16 has an aperture 20 formed therethrough. The cylindrical side wall 18 is comprised of a rigid interior layer 22 and a soft foam outer layer 24. The closed lower end 16 is comprised of a soft foam layer 24. The cylindrical member 12 has preferable dimensions of five inches in height and a diameter of four inches. The preferable construction of the rigid inner layer 22 is a PVC pipe while the soft foam outer layer 24 is designed with a camouflage appearance to further allow a hunter utilizing the device 10 to be disguised from his/her prey.

Next, the device 10 includes a circular mouth member 28 having an annular recess 30 formed in a lower surface thereof. The annular recess 30 is secured to the open upper end 14 of the cylindrical member 12. The circular mouth member 28 has an opening 32 therethrough. The circular mouth member 28 is designed to allow a hunter to comfortably press their mouth against it while coughing or sneezing into the cylindrical member 12.

The device 10 also includes a handle portion 36 having a generally U-shaped configuration. Free ends 38 of the handle portion 36 are secured to the cylindrical side wall 18 of the cylindrical member 12 upwardly of the closed lower end 16 thereof. The handle portion 36 allows the hunter to raise the cylindrical member 12 to place the circular mouth member 28 to their mouth when they need to cough or sneeze.

Lastly, the device 10 includes a noise suppressing portion 42 comprised of a planar member 44 having a plurality of apertures 46 formed therethrough. The planar member 44 has a short lower end 48 and a long upper end 50. The planar member 44 has a straight side edge 52 and an angular lower edge 54 whereby a width of the planar member 44 gradually increases from the short lower end 48 to the long upper end 50. The short lower end 48 has a disk member 56 secured thereto. The disk member 56 has a plurality of apertures 58 therethrough The noise suppressing portion 42 is dimensioned for placement within the hollow interior of the cylindrical member 12 with the planar member 44 in a spiraled configuration whereby the disk member 56 positioned within the aperture 20 in the closed lower end 16 of the cylindrical member 12. The planar member 44 is simply rolled up to be placed within the cylindrical member 12. The planar member 44 is constructed on a foam rubber material similar to the outer layer of the cylindrical side wall 18. The planar member 44 will serve to suppress the coughing or sneezing of the hunter thereby not scaring away the prey being hunted. The apertures 58 in the disk member 56 allow the breathed air from the hunter to slowly exit from the device 10 thereby limiting the noise.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A noise suppressor apparatus for reducing audible level of coughs, sneezes, or the like comprising, in combination:

a cylindrical member having an open upper end, a closed lower end, a cylindrical side wall therebetween, and a hollow interior, the closed lower end having an aperture formed therethrough, the cylindrical side wall being comprised of a rigid interior layer and a soft foam outer layer, the closed lower end being comprised of a soft foam layer;

a circular mouth member having an annular recess formed in a lower surface thereof, the annular recess secured to the open upper end of the cylindrical member, the circular mouth member having an opening therethrough;

a handle portion having a generally U-shaped configuration, free ends of the handle portion secured to the cylindrical side wall of the cylindrical member upwardly of the closed lower end thereof;

a noise suppressing portion comprised of a planar member having a plurality of apertures formed therethrough, the planar member having a short lower end and a long upper end, the planar member having a straight side edge and an angular lower edge whereby a width of the planar member gradually increases from the short lower end to the long upper end, the short lower end having a disk member secured thereto, the disk member having a plurality of apertures therethrough, the noise suppressing portion dimensioned for placement within the hollow interior of the cylindrical member with the planar member in a spiraled configuration whereby the disk member positioned within the aperture in the closed lower end of the cylindrical member.

2. A noise suppressor apparatus comprising:

a cylindrical member having an open upper end, a closed lower end, a cylindrical side wall therebetween, and a hollow interior, the closed lower end having an exposed aperture formed therethrough, the open upper end dimensioned for placement over a mouth of a coughing individual;

a noise suppressing portion dimensioned for placement within the hollow interior of the cylindrical member.

3. The apparatus as set forth in claim 2 wherein the cylindrical side wall of the cylindrical member being comprised of a rigid interior layer and a soft foam outer layer, the closed lower end being comprised of a soft foam layer.

4. The apparatus as set forth in claim 2 and further including a circular mouth member having an annular recess formed in a lower surface thereof, the annular recess secured to the open upper end of the cylindrical member, the circular mouth member having an opening therethrough.

5. The apparatus as set forth in claim 2 and further including a handle portion secured to the cylindrical member.

6. The apparatus as set forth in claim 5 wherein the handle portion having a generally U-shaped configuration, free ends of the handle portion secured to the cylindrical side wall of the cylindrical member upwardly of the closed lower end thereof.

7. The apparatus as set forth in claim 2 wherein the noise suppressing portion being comprised of a planar member having a plurality of apertures formed therethrough, the planar member having a short lower end and a long upper end, the planar member having a straight side edge and an angular lower edge whereby a width of the planar member gradually increases from the short lower end to the long upper end, the short lower end having a disk member secured thereto, the disk member having a plurality of apertures therethrough, the noise suppressing portion dimensioned for placement within the hollow interior of the cylindrical member with the planar member in a spiraled configuration whereby the disk member positioned within the aperture in the closed lower end of the cylindrical member.

* * * * *